United States Patent [19]

Covic et al.

[11] 4,071,771
[45] Jan. 31, 1978

[54] SHUTTERS FOR X-RAY SCANNERS

[75] Inventors: John Covic, Wickliffe; Thomas R. McBride, Chardon, both of Ohio

[73] Assignee: Ohio-Nuclear, Inc., Solon, Ohio

[21] Appl. No.: 700,538

[22] Filed: June 28, 1976

[51] Int. Cl.² .............................................. G21F 5/04
[52] U.S. Cl. ..................................... 250/505; 250/402; 250/445 T; 250/511; 250/514
[58] Field of Search ................ 250/505, 511, 512, 513, 250/514, 401, 402, 445 T

[56] References Cited

U.S. PATENT DOCUMENTS

| | | | |
|---|---|---|---|
| 3,275,831 | 9/1966 | Martin | 250/514 |
| 3,384,751 | 5/1968 | Sperry | 250/514 |

*Primary Examiner*—Craig E. Church
*Attorney, Agent, or Firm*—Fay & Sharpe

[57] ABSTRACT

Rotary safety shutter mechanisms for use in computerized tomographic X-ray scanners of the type wherein a source of radiation and a detector means are mounted for movement on opposite sides of a medium in order that the radiation passes through successive planar sections of medium and is attenuated and detected to give an output. The safety shutter mechanisms are arranged to be positioned adjacent the outlet aperture of the radiation source to selectively block the outlet upon occurrence of a predetermined condition. Two different embodiments of safety shutter mechanisms are disclosed. In each embodiment, the mechanism comprises a housing mounted adjacent the outlet aperture and having a through passage through which radiation from the source can pass. A cylindrical shutter member is carried in the housing transversely of the passage and mounted for rotary movement between a first position which permits the flow of radiation from the source and a second position which blocks the flow. In the first embodiment, the shutter member is moved from the second to the first position by a linear solenoid connected with the shutter member through a crank which is continually biased to move the shutter to the second position. In the second embodiment, the shutter member is actuated to the first position by a rotary solenoid aligned with the axis of rotation of the shutter member and directly coupled thereto.

9 Claims, 10 Drawing Figures

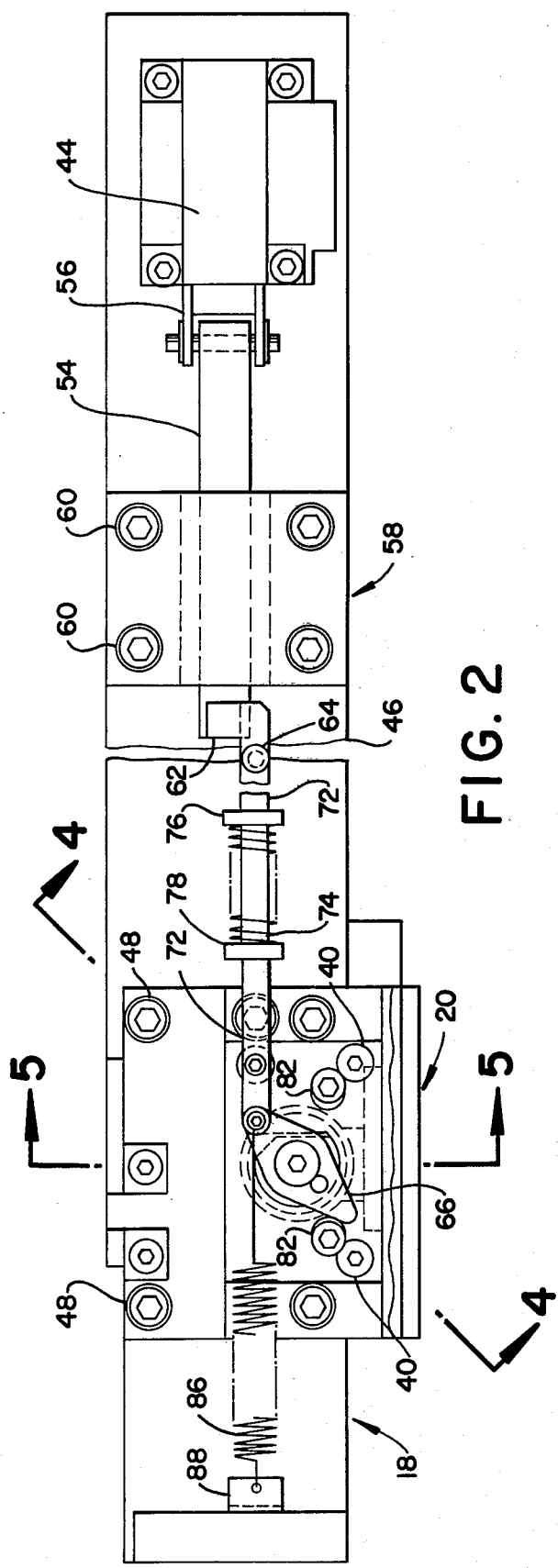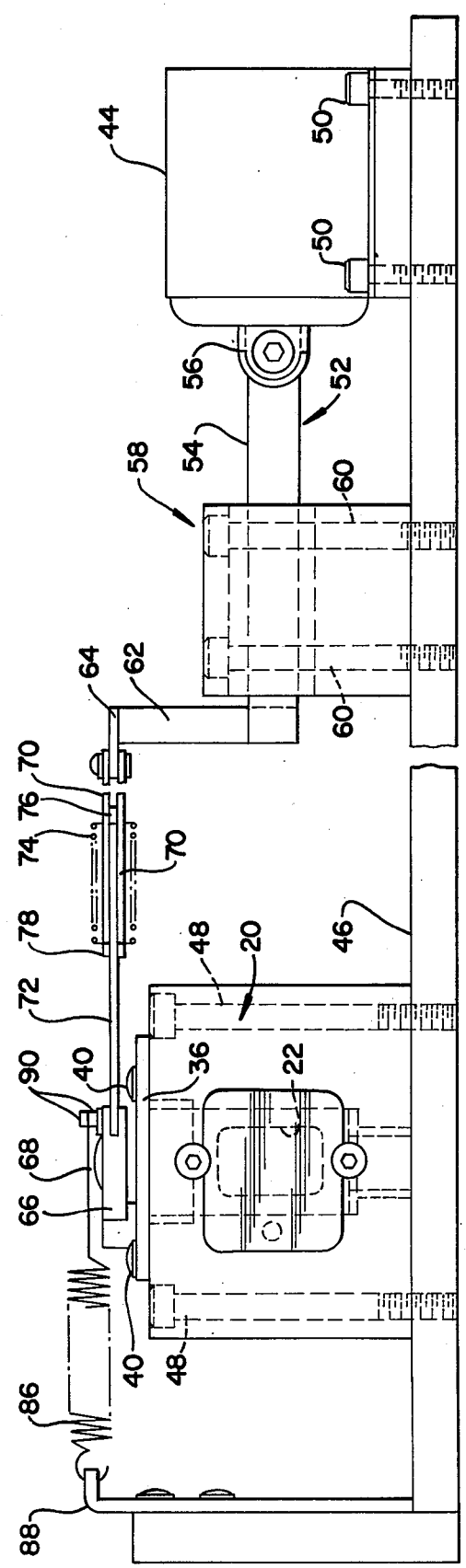

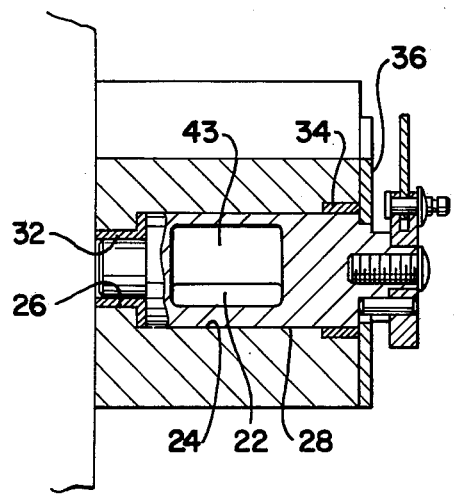
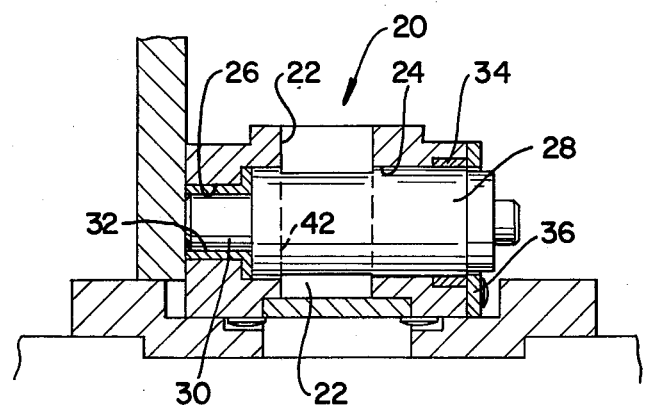
FIG. 4  FIG. 5
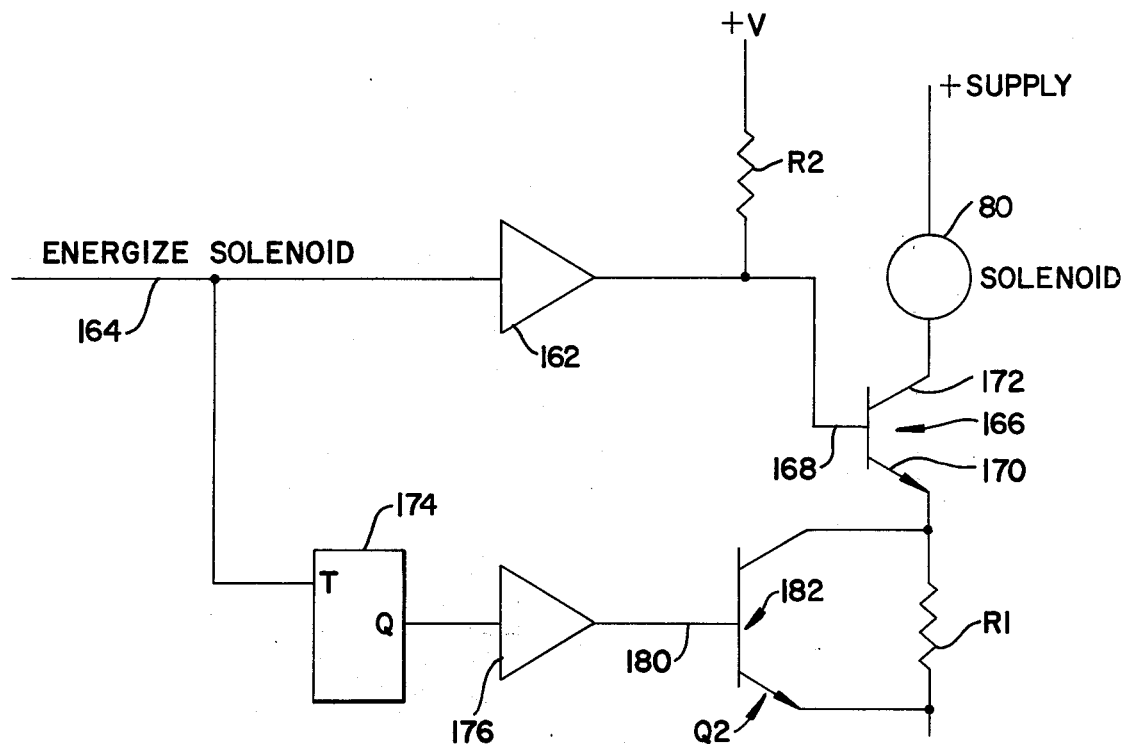
FIG. 10

SHUTTERS FOR X-RAY SCANNERS

BACKGROUND OF THE INVENTION

In the commonly-assigned, co-pending application entitled "Safety Control System for X-Ray Scanner", filed concurrently herewith, there is disclosed a safety control system for a computerized tomographic X-ray scanner of the type wherein a source of radiation and a detector means are mounted for movement on the opposite sides of a medium in order that the radiation passes through successive planar sections of the medium and is attenuated and detected to give an output. According to the system disclosed in the noted application, the safety control includes means responsive to the rate of movement of the source of radiation and the detector together with blocking means which are actuated to block the flow of radiation from the source when the rate of movement of the radiation source is below a predetermined minimum.

The noted system allows the X-ray tubes to be maintained under operating voltage and current throughout the examination procedure. Additionally, the system acts to prevent excessive X-ray exposure by the patient being scanned or the operating personnel even if the apparatus for moving the source malfunctions.

In the specific embodiment disclosed in the noted application, the blocking means comprises a flat plate shutter formed from lead. The flat plate shutter is mounted for sliding movement transverse to the X-ray tube outlet aperture through a direct connection with a linear solenoid. Although this particular arrangement is generally satisfactory, its speed of actuation and reliability is less than desirable in the safety system of the type under consideration.

BRIEF DESCRIPTION OF THE INVENTION

The subject invention provides a highly-reliable, fast-acting shutter mechanism particularly suited for use in a safety system of the type described. According to the subject invention, the shutter mechanism includes a housing mounted adjacent the outlet aperture of an X-ray tube assembly. The housing is provided with a through passage which is aligned with the outlet aperture. Mounted for rotation within the housing and extending transversely of the passage is a generally cylindrical shutter member rotatable from a first position which permits radiation to flow through the passage to a second position wherein the flow of radiation is blocked. The shutter member is maintained under a continual bias toward the second position. A solenoid is drivingly connected to the shutter member such that when energized it drives the shutter member to the first position against the biasing force. Upon de-energization, the biasing force returns the shutter member to the blocking position.

According to a more limited aspect of the invention, the solenoid is a linear solenoid connected to the shutter member through a crank. The biasing is accomplished by a spring connected to the crank and acting in opposition to the solenoid.

According to another aspect of the invention, the solenoid is a rotary solenoid directly coupled with the shutter member.

Also, according to the invention, apparatus of the general type described is coupled with safety means responsive to movement of the source of radiation and energizing the solenoid for moving the shutter member to a position for blocking the flow of radiation from the source when the rate of movement of the source is below a predetermined minimum.

Preferably, the safety means also include time-delay means which prevent movement of the blocking means to a blocking position until the rate of movement has been below the predetermined minimum for a predetermined time period. This allows the normal reversal in direction of movement of the source to take place at the end of each traverse without having the blocking means assume a blocking position.

According to another feature of the invention, selectively-operable means are provided for maintaining the rotary shutter member in blocking condition even when the rate of movement is above the predetermined rate. This prevents accidental scanning with the blocking means in a non-blocking condition.

BRIEF DESCRIPTION OF THE DRAWINGS

FIG. 2 is an enlarged view of the shutter portion of the FIG. 1 assembly;

FIG. 3 is a view taken on line 3—3 of FIG. 1;

FIGS. 4 and 5 are cross-sectional views taken on lines 4—4 and 5—5, respectively, of FIG. 2;

FIG. 10 shows a solenoid driver circuit.

DETAILED DESCRIPTION OF THE DRAWINGS

Figure 1:
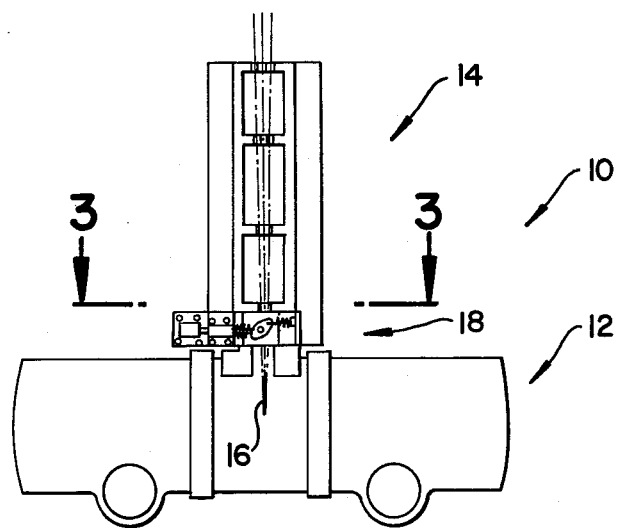
FIG. 1 is a view partially in cross-section showing a shutter mechanism formed in accordance with the invention mounted in an X-ray tube and collimator assembly.

FIG. 1 shows the overall arrangement of a typical X-ray tube and collimator assembly 10 of the type discussed. As illustrated, it includes a conventional X-ray tube 12 and a collimator 14. The X-ray tube 12 includes an outlet aperture 16 from which X-radiation is emitted. The X-radiation is collimated or formed into thin, pencil-like beams by the collimator 14. The general arrangement and use of this particular apparatus in a computerized tomographic scanner is more fully described in the commonly-assigned, co-pending application entitled "Safety Control System for X-Ray Scanner", filed concurrently herewith and incorporated herein by reference. Mounted adjacent the aperture 16 and between the X-ray tube 12 and the collimator 14 is a safety shutter mechanism 18 formed in accordance with the subject invention.

Referring in particular to FIGS. 2-5, it will be seen that the shutter mechanism 18 includes a generally rectangular housing 20 positioned adjacent the outlet 16. A rectangular passageway 22 is formed through the housing 20 and aligned with the outlet 16 so that X-radiation can pass through the housing 20 to the collimator 14. Extending transversely of the passage 22 is a cylindrical bore 24 having a reduced diameter inner end portion 26. Rotatably mounted within the bore 24 is a generally cylindrical shutter member 28. As shown, shutter member 28 includes a reduced diameter end portion 30 which is received in the correspondingly-reduced diameter end portion 26 of bore 24. Suitable bearings 32 are provided at the inner end of the bore. A similar sleeve-type bearing 34 is received about the outer end of bore 24. As shown, the shutter member 28 is maintained in the bore while being permitted to rotate freely relative thereto by a retainer plate 36 suitably connected to the housing 20 by socket head machine screws 40.

Extending transversely through the rotary shutter member 28 is an opening 42 sized and shaped to correspond generally with the opening 22 of housing 20. As can be appreciated, with the opening 42 aligned with the passage 22 X-radiation from the X-ray tube assembly 12 is permitted to pass through the passage 22. However, upon rotation of the shutter member 28 to a position angularly spaced 90 degrees from the aligned position, the flow of X-radiation through the passageway is blocked.

The actuating means for moving the shutter between the blocking and non-blocking positions includes a linear solenoid member 44. The solenoid 44 and the shutter housing 20 are carried from a common base plate 46. As best seen in FIG. 3, the housing member 20 is releasably connected to the base 46 by a plurality of machine screws 48. Similarly, the solenoid 44 is connected to the base plate 46 by screws 50. The output shaft of solenoid 44 is drivingly connected with the shutter member 28 by a drive connection assembly 52. As shown, the drive connection assembly 52 includes a first reciprocably mounted shaft 54 suitably pinned to the plunger 56 of solenoid 44. The shaft 54 is reciprocably mounted in a guide block assembly 58. As shown, the guide block assembly 58 is connected to the base plate 46 by machine screws 60. At the outer free end of shaft 54, there is connected a vertically-extending, rectangular rod 62 having a laterally-extending end portion 64. The end portion 64 is drivingly-connected with a crank member 66 affixed to the outer end of the rotary shutter member 28 by a screw 68. As shown, a first pair of parallel-spaced bars 70 are pinned or otherwise pivotally-connected to the plate 64 and engage on opposite sides of a plate or bar 72 which is suitably pinned to one end of the crank member 66 (see FIG. 2). The plates 70 are drivingly connected with plates 72 through a cylindrical compression spring 74 which is mounted between tabs 76 and 78 formed on the ends of plates 70 and 72, respectively. This arrangement allows energization of the solenoid 44 to pull the crank 66 and rotate the rotary shutter member 28 to the solid-line, non-blocking position shown in FIGS. 2-4. The compression spring 74 permits the total movement of the shutter to be adjusted without varying the stroke length of the solenoid. Note that the compression spring 74 can merely compress to allow the full stroke length of the solenoid without requiring a corresponding linear movement of the end of the crank 66.

The movement of crank 66 is limited by a pair of adjustable eccentric screws 82 extending outwardly from the housing 20. The screws 82 are positioned to engage the outwardly-extending end of crank 66. By rotating the screws 82, fine adjustment of the stop positions can be achieved.

The rotary shutter member 28 is maintained under a continual bias tending to move it to the blocking position. For this reason, a tension spring 86 extends between a vertically-extending end plate 88 and the crank 66. As shown, one end of spring 86 is connected to a vertically-extending pin 90 which is carried on the end of crank 66. Consequently, upon de-energization of solenoid 44 spring 86 retracts and rotates the shutter member 28 to the blocking position.

Figure 6:
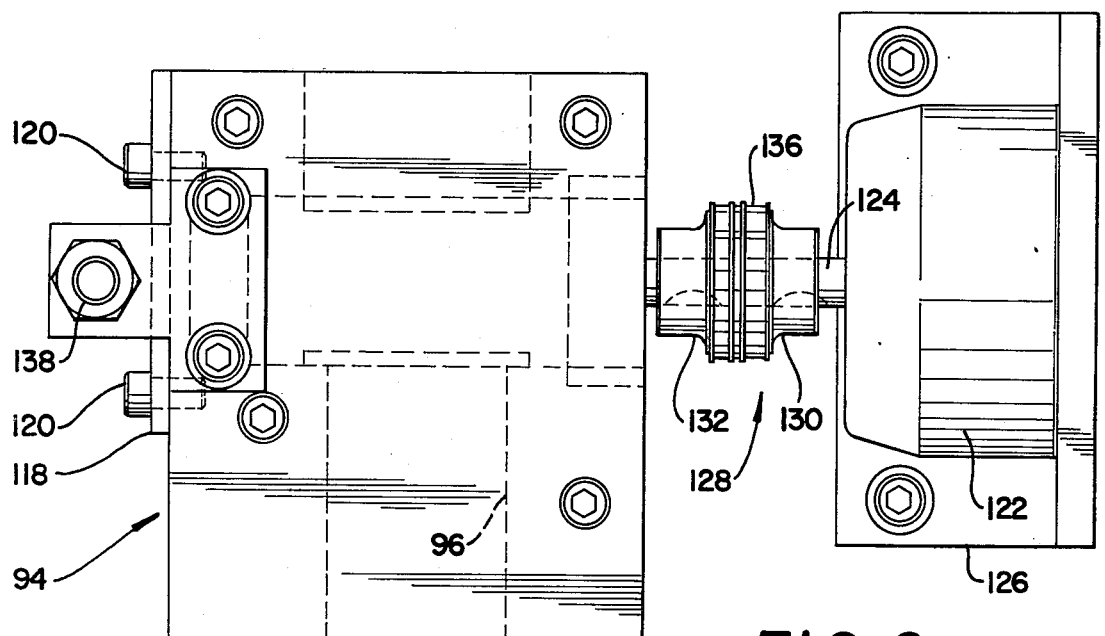
FIG. 6 is a view similar to FIG. 2 but showing a modified form of rotary shutter mechanism.
Figure 7:
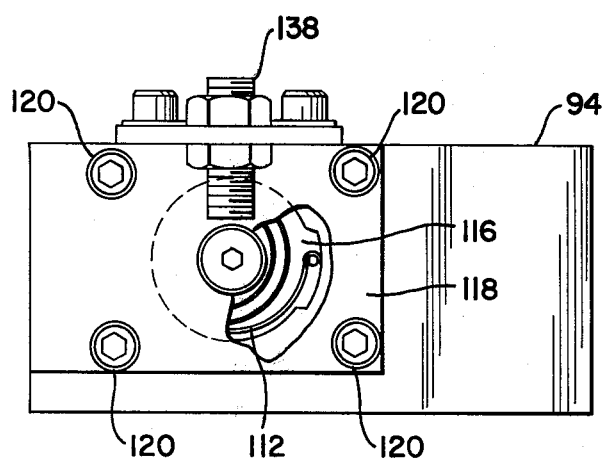
FIG. 7 is a view taken on line 7—7 of FIG. 2.
Figure 8:
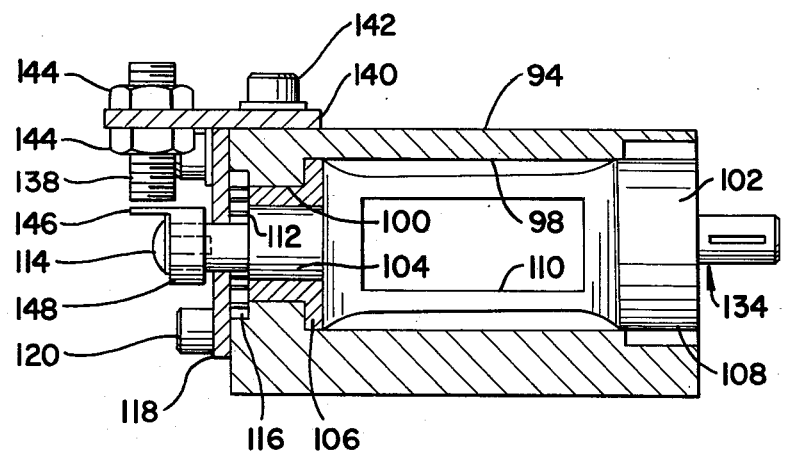
FIG. 8 is a cross-sectional view taken on line 8—8 of FIG. 7.

FIGS. 6-8 show a second embodiment of a rotary shutter mechanism formed in accordance with the subject invention. As illustrated therein, the mechanism includes a generally-rectangular housing 94 provided with a through passage 96 adapted to permit the passage of X-radiation from the X-ray tube assembly 12 to the collimator 14. Extending through the housing transversely of the passage 96 is a cylindrical bore 98 (see FIG. 8). The bore 98 has a reduced diameter end portion 100. Positioned within the bore and mounted for rotation therein is a generally cylindrical rotary shutter member 102. As shown, the shutter member 102 has a reduced diameter inner end portion 104 which is received in a suitable sleeve bearing 106 carried in the reduced diameter end 100 of bore 98. A second sleeve bearing 108 is received in a counterbore formed at the opposite end of bore 98.

Extending transversely through the rotary shutter member 102 is a generally-rectangular opening 110. Opening 110 is sized and positioned so that when the shutter member 102 is rotated to the solid-line position shown in FIG. 8, opening 110 is aligned with the passageway 96 to permit the X-radiation to pass from the X-ray tube assembly to the collimator. However, when rotated 90 degrees beyond the non-blocking position, the shutter member acts to prevent the flow or passage of radiation through passageway 96.

The rotary shutter member 102 is maintained under a continual biasing force acting to move it to the blocking position. In the subject embodiment, the biasing means comprise a flat coil spring 112 which surrounds a stub shaft 114 extending from the rotary shutter member 102. As shown, the spring 112 is received within a recess 116 formed in the left end of housing 94 as viewed in FIG. 8. The inner end of spring 112 is positively connected to stub shaft 114 and the outer free end is pinned to the housing 94 as best shown in FIG. 7. The spring member 112 is maintained in position in the recess by a retaining cover plate 118 connected to the housing by suitable machine screws 120.

In the subject embodiment, the shutter member is moved to its non-blocking position against the bias of spring 116 by a rotary solenoid 122. The solenoid 122 is carried with its output shaft 124 extending parallel to the axis of rotation of the rotary shutter member 102. As best illustrated in FIG. 6, the solenoid 122 is carried from a generally L-shaped support bracket 126 mounted on a common base plate 128 with the housing 94. The output shaft 124 of solenoid 122 is drivingly connected with the rotary shutter member 102 by a chain drive connection 128 including a first sprocket 130 keyed or otherwise positively connected to shaft 124. A second sprocket 132 is similarly connected to a stub shaft 134 extending outwardly from rotary shutter member 102. A chain 136 is trained about the sprockets to transmit the rotary motion from the solenoid to the rotary shutter member.

Means are provided to produce an output signal indicative of the position of the rotary shutter member 102. In the subject embodiment, these means comprise a proximity switch 138 carried at the left-hand end of housing 94 as viewed in FIG. 8. The proximity switch 138 is carried from a support plate 140 extending outwardly from housing 94 and connected thereto by socket screws 142. Adjustment of the position of the proximity switch 138 is provided by a pair of nuts 144 threadedly received on the exterior of the switch and engaged on opposite sides of the mounting plate 140.

As best shown in FIGS. 7 and 8, the proximity switch 138 is arranged to sense the presence of a small metal tab 146 which extends outwardly from a sleeve or cap member 148 connected to the end of the stub shaft 114. Consequently, during rotation of the shutter member 102 between the blocking and non-blocking position, the tab portion 146 is moved from a laterally-spaced position to a position directly adjacent the lower end of the proximity switch 138.

Figure 9:
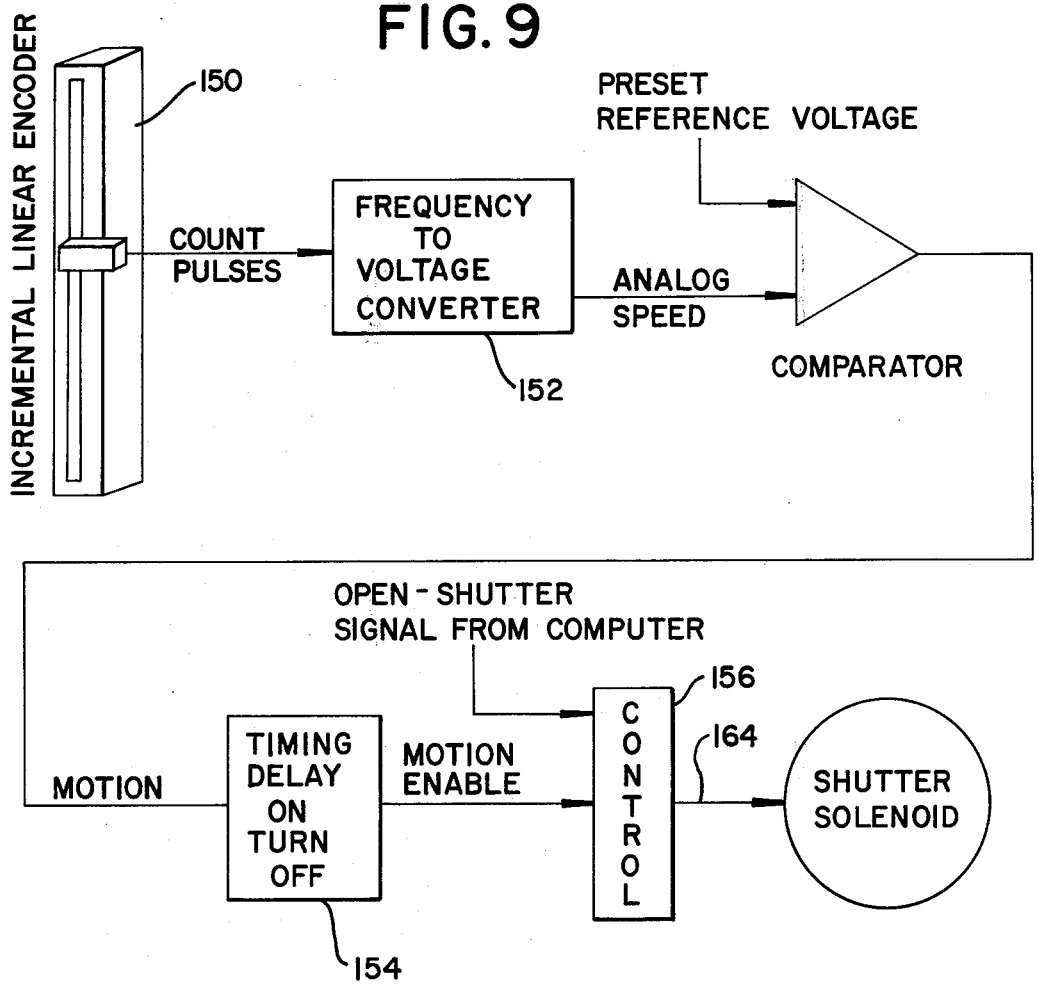
FIG. 9 is a block diagram showing the blocking means control system.

Control of the solenoids in either of the above embodiments is effected by a safety means shown in FIGS. 9 and 10. This control system permits energization of the solenoids only after a scan frame (not shown) supporting the radiation has reached a predetermined scan velocity. In particular, it includes a linear encoder 150 which is mechanically coupled to the scan frame. As the frame traverses, the encoder 150 produces a train of electrical output pulses having a frequency which is directly proportional to the speed of the frame. Many different types of encoders could be used for this purpose.

The output pulses are directed to a conventional frequency to voltage converter 152 which converts them to an analog output. The analog output voltage is compared with a pre-set reference voltage which corresponds to the minimum speed of the scan frame at which the blocking means is designed to open.

Item 154 is a timing delay which is operative only on de-energizing the solenoid whenever the frame speed drops below the pre-set value. Consequently, the timing delay keeps the solenoid energized and the shutter member in its non-blocking position at the end of the traverse cycle. This is done in order to achieve adequate reliability and life of the shutter plate mechanism.

From the time delay 154, a motion enable signal is directed to an and-gate 156. Control 158 requires two other conditions to be true before the solenoid is energized. Specifically, the operator has a protective key-actuated switch 160 on the scanner control console (not shown). The switch allows the operator to prevent accidental scanning with an open shutter while attending to or re-positioning a patient on the scanner table. Control 158 also requires a second condition in that the computer program must have instructed the shutter plate to open at the desired time in the scanner control program.

FIG. 10 shows a solenoid driver circuit which is designed to provide the required high current to energize the solenoid while maintaining a holding current below the continuous solenoid rating. It also eliminates A.C. magnetic flux from the solenoid due to power supply ripple by providing pure D.C. Moreover, the circuit allows full high current pull-in at any time after the solenoid has been released and will not overheat the solenoid if the plunger becomes stuck. When the line 164 for energizing the solenoid goes true, i.e. an actuation signal is transmitted, the signal is received by a buffer amplifier 162. When such a signal occurs, the transistor 166 having base 168, emitter 170 and collector 172, is in effect turned on and conducts. The base 168 is charged positively by a positive voltage source of about 15 volts through a resistor R2. The resistor may have a range of about 100 ohms to 10K and is usally in the area of about 1K. The transistional section or the rising edge of the energized solenoid signal also actuates a monostable 174. In its actuated state, the signal passes through the monostable 174 through a buffer amplifier 176 to the base 180 of a transistor 182. The transistor 182 then conducts and shorts out the transistor 166 emitter resistor. This saturates transistor 182 thereby applying the full voltage from a positive supply 112 across the solenoid and provides a high current for actuating the solenoid. When the monostable 174 is not actuated, the transistor 182 does not conduct current and current through the solenoid drops to a value determined by the positive voltage (about 15 volts) and the resistor R1. In this stage, the transistor 166 provides a constant current source to the solenoid that is independent of the ripple voltage on the positive supply 112. Anytime the "energized solenoid" signal goes fault, i.e. an actuation signal is not applied, the transistor 166 turns off stopping all current through the solenoid.

This invention has been described with reference to the preferred embodiment with some possible modifications thereto. For example, this invention could also be utilized with other radiation, such as gamma radiation. Moreover, the shutter mechanisms could be utilized in other devices. Obviously, other modifications and alterations will be obvious to others upon the reading and understanding of this specification. It is our intention to include all such modifications and alterations insofar as they come within the scope of the appended claims or the equivalents thereof.

The invention claimed is:

1. A safety shutter mechanism for use in an X-ray scanner of the type wherein a source of radiation and a detector means are mounted for movement on opposite sides of a medium in order that the radiation passes through successive planar sections of medium and is attenuated and detected to give an output, comprising:
   a housing adapted to be positioned adjacent the outlet aperture of the radiation source and having a passage through which can pass radiation leaving the outlet aperture and a generally cylindrical bore extending transversely to said passage;
   a generally cylindrical shutter means rotatably mounted in said bore for selective arcuate movement between a first position which permits radiation to pass through said passage and a second position which blocks the flow of radiation through said passage;
   biasing means engaging said shutter member and acting to continually bias said member toward the second position; and,
   a rotary solenoid aligned with and drivingly connected with said shutter member for selectively moving said shutter member to said first position against said biasing means said rotary solenoid being operatively connected to the source of radiation so that it is actuated by a predetermined condition of movement of the source.

2. The safety shutter mechanism of claim 1 wherein said biasing means comprises a spring member engaging an end portion of said shutter member.

3. The safety shutter mechanism of claim 1 including adjustable means for limiting the rotary movement of said shutter member.

4. In an apparatus for measuring the attentuation of radiation after passage through a medium for reconstructing a representation of the medium, the apparatus including a movable source of radiation mounted to facilitate the passage of radiation therefrom through the medium and a detector means for the radiation on the side of the medium opposite the source of radiation, the improvement comprising:

safety means responsive to the rate of movement of the source of radiation and including blocking means for blocking the flow of radiation from the source when the rate of movement of the source is below a predetermined minimum, the blocking means including a housing having a passage therethrough through which the radiation may pass, a generally cylindrical bore extending generally transversely to the passage and a generally cylindrical shutter member rotatably mounted in the bore for arcuate movement between a first position which permits radiation to pass through said passage and to a second position where it blocks the flow of radiation through said passage, and a rotary solenoid directly coupled to said shutter member.

5. The apparatus of claim 4 wherein the safety means comprises an incremental linear encoder operatively connected to the movement of the source of radiation, a comparator for comparing the speed of the source of radiation with a reference voltage.

6. The apparatus as defined in claim 5 wherein said safety means further includes a time delay means for preventing operation of the blocking means until the rate of movement of the source is below the predetermined minimum for a predetermined period of time.

7. The apparatus as defined in claim 6 wherein the safety means further includes means for providing current to energize the solenoid, the means for providing current including a circuit means operatively attached to the solenoid, the circuit means including a first conductor operable upon a preset signal and a second conductor operable upon the same signal so that the conduction occurs in the circuitry to the solenoid.

8. The apparatus as defined in claim 7 wherein the first conductor is a first transistor and the second conductor is a second transistor so that upon the preset signal current is conducted through the first transistor and second transistor without an appreciable voltage drop.

9. The apparatus as defined in claim 8 wherein the second transistor has its base operatively connected to a monostable switch which when activated to an activated state permits conduction therethrough thus biasing the base of the second transistor.

* * * * *